United States Patent [19]

Arhancet

[11] Patent Number: 5,886,241
[45] Date of Patent: Mar. 23, 1999

[54] METHODS AND COMPOSITIONS FOR INHIBITING THE POLYMERIZATION OF ETHYLENICALLY UNSATURATED MONOMERS

[75] Inventor: Graciela B. Arhancet, Katy, Tex.

[73] Assignee: BetzDearborn Inc., Trevose, Pa.

[21] Appl. No.: 63,457

[22] Filed: Apr. 21, 1998

Related U.S. Application Data

[63] Continuation-in-part of Ser. No. 642,836, May 3, 1996, Pat. No. 5,756,870.

[51] Int. Cl.$^6$ .............................. C07C 7/20; B01D 3/00; C09K 15/08; C10G 9/12
[52] U.S. Cl. .................................. 585/2; 585/3; 585/24; 203/9; 252/404; 208/48 R; 208/48 AA
[58] Field of Search ................... 585/2, 3, 24; 203/9; 252/404; 208/48 R, 48 AA

[56] References Cited

U.S. PATENT DOCUMENTS

| | | | |
|---|---|---|---|
| 2,388,041 | 10/1945 | Craig | 203/9 |
| 2,473,203 | 6/1949 | Howe | 203/9 |
| 3,510,405 | 5/1970 | Takao et al. | 209/9 |
| 3,775,493 | 11/1973 | DeSimone et al. | 203/9 |
| 3,951,754 | 4/1976 | Liakumovich et al. | 203/9 |
| 4,439,278 | 3/1984 | Douglas et al. | 203/9 |
| 4,596,655 | 6/1986 | Van Eijl | 203/9 |
| 4,725,628 | 2/1988 | Garvey et al. | 521/137 |
| 5,043,504 | 8/1991 | Bedell | 585/3 |
| 5,396,005 | 3/1995 | Arhancet | 585/3 |
| 5,416,258 | 5/1995 | Arhancet et al. | 585/3 |
| 5,756,870 | 5/1998 | Arhancet | 585/2 |

FOREIGN PATENT DOCUMENTS

| | | | |
|---|---|---|---|
| 961863 | 1/1975 | Canada | 203/9 |
| 163428 | of 1974 | Czechoslovakia | C08F 1/02 |
| 89402165 | of 1989 | European Pat. Off. | |
| 59015477 | of 1982 | Japan. | |
| 1098200 | of 1982 | U.S.S.R. | C07C 07/20 |

*Primary Examiner*—Mark L. Bell
*Assistant Examiner*—Patricia L. Hailey
*Attorney, Agent, or Firm*—Alexander D. Ricci; Philip H. Von Neida

[57] ABSTRACT

The polymerization of an ethylenically unsaturated monomer such as isoprene, butadiene and acrylonitrile is inhibited during storage or handling thereof by the addition of a dihydroxycinnamic acid or derivative thereof.

7 Claims, No Drawings

METHODS AND COMPOSITIONS FOR INHIBITING THE POLYMERIZATION OF ETHYLENICALLY UNSATURATED MONOMERS

This application is a continuation-in-part of Ser. No. 08/642,836, filed May 3, 1996, now U.S. Pat. No. 5,756,870.

FIELD OF THE INVENTION

This invention relates to methods and compositions for inhibiting polymerization of ethylenically unsaturated monomers. The methods are particularly effective at inhibiting polymerization of these monomers during storage conditions in the presence of oxygen.

BACKGROUND OF THE INVENTION

It is well known that ethylenically unsaturated monomers readily polymerize when heated and that the polymerization rate increases with increasing temperature. For this reason, the monomers are stabilized by the addition of substances which act as inhibitors or retarders of polymerization, or which block the initiation mechanism leading to the formation of radicals.

Certain ethylenically unsaturated (diolefin) monomers such as butadiene and isoprene polymerize when left in storage tanks and during transportation at temperatures as low as room temperature. This polymerization is initiated by reaction of the diolefin monomer with oxygen present in the monomer containing system. This reaction forms peroxides and free radical species which can further react with the diolefin monomer.

To prevent this polymerization from taking place, diolefin monomer manufacturers frequently add tert-butyl catechol (TBC) as a polymerization inhibitor. However, TBC is a toxic compound and can cause tissue damage when it contacts skin. These characteristics make it desirable to utilize an inhibitor compound that avoids these difficulties as well as being water and caustic extractable so that it could be easily removed from the finished product before use or additional processing.

The present inventor has discovered that dihydroxycinnamic acid and its derivatives effectively inhibit the polymerization of ethylenically unsaturated monomers during storage and transportation. These compounds prove particularly effective in the presence of oxygen and at temperatures up to 100° C.

DESCRIPTION OF THE RELATED ART

EP 89-402156 discloses a cosmetic preparation containing an antioxidant system based on a stabilized ascorbic acid ester. The antioxidant system also contains tocopherol or mixtures of tocopherol, caffeic acid or its derivatives, a complexing agent and a non-thiol polypeptide.

JP Kokai JP 59015477 teaches a food antioxidant composition effective for oils and fats which comprises 3,4-dihydroxycinnamic acid esters and one or more of ascorbic acid-stearic acid ester, citric acid, malic acid, and ascorbic acid.

DETAILED DESCRIPTION OF THE INVENTION

The present invention relates to methods and compositions for inhibiting the polymerization of ethylenically unsaturated monomers comprising adding an effective inhibiting amount of a dihydroxycinnamic acid or derivative thereof.

The dihydroxycinnamic acid or derivatives thereof generally have the formula:

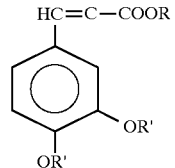

wherein R is H, $CH_3$ or $C_2H_5$; R is H, $CH_3$ or $C_2H_5$ with the proviso that at least one of R' is H. The preferred compounds for use in the present invention are dihydroxycinnamic acid and dihydroxydihydrocinnamic acid.

The dihydroxycinnamic acid or derivatives thereof are effective at inhibiting the polymerization of ethylenically unsaturated monomers during their storage or under transportation conditions. These conditions are typically found to have oxygen atmospheres present and monomer temperatures up to about 100° C. The present inventor anticipates that the methods of the present invention can inhibit the polymerization of ethylenically unsaturated monomers during the processing thereof. These processing conditions, such as purification and distillation processes, typically employ heat and will often cause fouling of the monomer.

The ethylenically unsaturated monomers are characterized as polymerizable ethylenically unsaturated hydrocarbons and include olephins such as alpha olephins containing 2 to 20 carbon atoms and preferably 2 to 8 carbon atoms, and conjugated di-olephins, preferably those containing 3 to 6 carbon atoms such as isoprene, butadiene and acrylonitrile.

For purposes of this invention, the term "effective amount" refers to the amount of dihydroxycinnamic acid or derivative thereof necessary to inhibit polymerization of ethylenically unsaturated monomers. This amount will vary according to the conditions under which the ethylenically unsaturated monomer is subjected during storage and/or handling thereof. At higher temperatures and higher monomer contamination, larger amounts of polymerization inhibiting compound are generally required.

Preferably the effective amount of dihydroxycinnamic acid or derivative added to the ethylenically unsaturated monomer ranges from about 1 part to about 1000 parts per million parts of monomer. More preferably, the amount of dihydroxycinnamic acid or derivative thereof added to the monomer ranges from about 10 parts to about 200 parts per million parts monomer.

The dihydroxycinnamic acid derivatives may be used in combination with the dihydroxycinnamic acid or as a mixture of the dihydroxycinnamic acid derivatives when utilized in the methods of the present invention.

The dihydroxycinnamic acid or derivative thereof may be added to the ethylenically unsaturated monomer as either a dispersion or as a solution using a suitable liquid carrier or solvent. Any solvent that is compatible with the dihydroxycinnamic acid or derivative thereof and the ethylenically unsaturated monomer may be employed.

The invention will now be described with reference to a number of specific examples which are to be regarded solely as illustrative, and not as restricting the scope of the invention.

EXAMPLES

A Testing was performed to determine the effectiveness of the present invention at inhibiting the polymerization of ethylenically unsaturated monomers.

Tests were run in a stainless steel pressure vessel fitted with a glass sample container and cover, a stem, a pressure gauge with a continuous recorder, and the appropriate valves and fittings. A solution of 10 mL of isoprene in 40 mL of heptane and the designated treatment were placed in the glass sample container and inside the pressure vessel. The vessel was closed, filled with oxygen at 100 psig and heated in a water bath at 100° C. The pressure was recorded continuously until a break point in the pressure-time curve (i.e., steepest slope of the curve) was reached. The induction time was calculated as the time elapsed between the placing of the vessel in the bath and the breaking point. The results of this testing are reported in Table I.

TABLE I

Polymerization Inhibition Testing

| Treatment | Dose (ppm) | Induction Time (min.) |
|---|---|---|
| Blank | — | 25 |
| TBC | 10 | 40 |
| BHT | 10 | 31 |
|  | 40 | 32 |
| DHHCA | 10 | 85 |
|  | 25 | 144 |
| Blank | — | 21 |
| TBC | 40 | 90 |
| DHHCA | 40 | 110 |
| DHCA | 40 | 54 |
| Blank | — | 25 |
| DHCA | 50 | 102 |
|  | 100 | 127 |

TBC is tert-butyl catechol
BHT is 2,6-di-t-butyl-4-methylphenol
DHCA is 3,5-dihydroxycinnamic acid
DHHCA is 3,4-dihydroxyhydrocinnamic acid These results demonstrate that the compounds of the present invention are effective at inhibiting the polymerization of ethylenically unsaturated monomers under conditions approximating storage. The commercially available inhibitors, TBC and BHT proved less effective than the inventive compounds.

Further testing was performed using a different ethylenically unsaturated monomer. 10 mL of uninhibited acrylonitrile was placed in a 50 mL pressure glass tube fitted with a stopper. The desired treatment was added and the tube was closed and immersed in an oil bath heated at 110° C. Every 30 minutes, tubes were inspected for turbidity or presence of polymer and the time elapsed was recorded. These results are presented in Table II.

TABLE II

Polymerization Inhibition Testing

| Treatment | Dose (ppm) | Induction Time (min.) |
|---|---|---|
| Blank | — | 60 |
| DHHCA | 5 | 930 |
| DHHCA | 1 | 270 |

DHHCA is 3,4-dihydroxyhydrocinnamic acid

As these results demonstrate, 1 ppm of the dihydroxycinnamic acid derivative proved effective at inhibiting the polymerization of an ethylenically unsaturated monomer under near storage conditions.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of ethylenically unsaturated monomers selected from the group consisting of isoprene and acrylonitrile comprising adding to the monomers an effective polymerization inhibiting amount of a dihydroxycinnamic acid or derivative thereof having the formula:

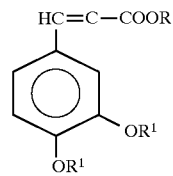

wherein R is H, $CH_3$ or $C_2H_5$; $R^1$ is H, $CH_3$ or $C_2H_5$ with the proviso that at least one of $R^1$ is H.

2. The method as claimed in claim 1 wherein said dihydroxycinnamic acid or derivative thereof is selected from the group consisting of dihydroxycinnamic acid and dihydroxydihydrocinnamic acid.

3. The method as claimed in claim 1 wherein said dihydroxycinnamic acid or derivative thereof is added to said monomers in an amount ranging from about 1 part to about 1000 parts per million parts of monomer.

4. The method as claimed in claim 1 wherein said monomer is exposed to oxygen atmospheres.

5. The method as claimed in claim 1 wherein said monomer has a temperature ranging from ambient to about 100° C.

6. A composition comprising an ethylenically unsaturated monomer selected from the group consisting of isoprene and acrylonitrile and a dihydroxycinnamic acid or derivative thereof having the formula:

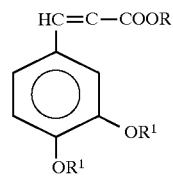

wherein R is H, $CH_3$ or $C_2H_5$; $R^1$ is H, $CH_3$ or $C_2H_5$ with the proviso that at least one of $R^1$ is H.

7. The composition as claimed in claim 6 wherein said dihydroxycinnamic acid or derivative thereof is selected from the group consisting of dihydroxycinnamic acid and dihydroxydihydrocinnamic acid.

* * * * *